(12) United States Patent
Childress

(10) Patent No.: US 10,264,931 B2
(45) Date of Patent: Apr. 23, 2019

(54) HAND DRYING SYSTEMS AND METHODS

(71) Applicant: THE BOEING COMPANY, Chicago, IL (US)

(72) Inventor: Jamie Childress, Mercer Island, WA (US)

(73) Assignee: The Boeing Company, Chicago, IL (US)

( * ) Notice: Subject to any disclaimer, the term of this patent is extended or adjusted under 35 U.S.C. 154(b) by 299 days.

(21) Appl. No.: 15/273,814

(22) Filed: Sep. 23, 2016

(65) Prior Publication Data

US 2018/0084956 A1 Mar. 29, 2018

(51) Int. Cl.
| | |
|---|---|
| *A61L 9/20* | (2006.01) |
| *A47K 10/48* | (2006.01) |
| *B64D 11/02* | (2006.01) |

(52) U.S. Cl.
CPC ............... *A47K 10/48* (2013.01); *A61L 9/20* (2013.01); *B64D 11/02* (2013.01)

(58) Field of Classification Search
CPC ............ A47K 10/48; A61L 9/20; B64D 11/02
USPC ............................................ 34/429, 90, 487
See application file for complete search history.

(56) References Cited

U.S. PATENT DOCUMENTS

| | | | | |
|---|---|---|---|---|
| 4,785,162 A | * | 11/1988 | Kuo | A45D 20/16 219/213 |
| 4,819,276 A | | 4/1989 | Stevens | |
| 5,568,691 A | * | 10/1996 | Rubin | A45D 20/16 34/98 |
| 5,641,421 A | * | 6/1997 | Manov | F24H 3/002 148/403 |
| 6,038,786 A | * | 3/2000 | Aisenberg | A47K 10/48 34/202 |
| 7,614,160 B2 | * | 11/2009 | Kameishi | A47K 10/48 34/90 |
| 7,774,953 B1 | * | 8/2010 | Duran | A47K 10/48 239/54 |
| 7,946,055 B2 | * | 5/2011 | Churchill | A47K 10/48 134/26 |
| 8,079,156 B1 | * | 12/2011 | Parish | F26B 21/008 15/320 |

(Continued)

FOREIGN PATENT DOCUMENTS

| | | | | |
|---|---|---|---|---|
| GB | 2434094 A | * | 7/2007 | ............. A47K 10/48 |
| RU | 2145178 C1 | * | 2/2000 | ............. A45D 20/16 |

(Continued)

OTHER PUBLICATIONS

Google search regarding how magnetic motor works on Dec. 26, 2018.*

(Continued)

*Primary Examiner* — Stephen M Gravini
(74) *Attorney, Agent, or Firm* — Joseph M. Butscher; The Small Patent Law Group, LLC

(57) ABSTRACT

A hand drying system and method for a lavatory includes a blower housing that includes a blower that is configured to generate airflow within an air chamber. An exhaust vent is configured to be secured to the lavatory. The exhaust vent defines an air outlet. A conduit includes a first end in fluid communication with the air chamber and a second end in fluid communication with the air outlet. The conduit distally locates the blower housing from the lavatory.

19 Claims, 7 Drawing Sheets

(56) References Cited

U.S. PATENT DOCUMENTS

| | | | | |
|---|---|---|---|---|
| 8,136,262 B2* | 3/2012 | Collins | A47K 10/48 | 34/105 |
| 8,201,344 B2* | 6/2012 | Sawabe | A47K 10/48 | 132/73.5 |
| 8,341,853 B2* | 1/2013 | French | A47K 10/48 | 15/300.1 |
| 8,490,291 B2* | 7/2013 | Churchill | A47K 10/48 | 222/1 |
| 8,813,383 B2* | 8/2014 | Liu | A47K 10/48 | 15/97.1 |
| 9,057,560 B2* | 6/2015 | Dyson | F26B 21/004 | |
| 9,060,657 B2* | 6/2015 | Ryan | A47K 10/48 | |
| 9,125,533 B2* | 9/2015 | Babikian | A47K 10/485 | |
| 9,441,885 B2* | 9/2016 | Bayley | A47K 4/00 | |
| 9,538,886 B2* | 1/2017 | Ros Marin | A47K 10/48 | |
| 9,695,546 B2* | 7/2017 | Lee | D06F 58/24 | |
| 9,743,812 B2* | 8/2017 | Courtney | A47K 10/48 | |
| 9,826,865 B2* | 11/2017 | Maruyama | G01F 23/268 | |
| 2014/0115764 A1 | 5/2014 | Cheng | | |
| 2018/0030701 A1* | 2/2018 | Bayley | E03C 1/01 | |
| 2018/0078101 A1* | 3/2018 | Satermo | A47K 10/48 | |

FOREIGN PATENT DOCUMENTS

| | | | | |
|---|---|---|---|---|
| WO | WO 9610349 A1 * | 4/1996 | | A45D 20/16 |
| WO | WO 9953250 A1 * | 10/1999 | | A47K 10/48 |
| WO | WO 2014036217 | 3/2014 | | |

OTHER PUBLICATIONS

How Electric Motors Work by Marshall Brain dated 2001 (from figure copyright).*

"Hand Dryers—Not Just Hot Air," Plumbing Connection.com, http://plumbingconnection.com.au/hand-dryers-not-just-hot-air/ (printed Sep. 19, 2016).

* cited by examiner

HAND DRYING SYSTEMS AND METHODS

FIELD OF THE DISCLOSURE

Examples of the present disclosure generally relate to hand drying systems and methods, and, more particularly, to efficient and quiet hand drying systems and methods that are particularly well suited for use within lavatories onboard vehicles, particularly commercial aircraft.

BACKGROUND OF THE DISCLOSURE

Commercial aircraft are used to transport passengers between various locations. A typical commercial aircraft includes one or more lavatories within an internal cabin.

A typical lavatory onboard an aircraft includes a sink and a faucet, by which individuals may wash their hands. Paper towels are provided so that the hands may be dried after washing. Used paper towels are discarded into a trash receptacle and, as such, generate a significant amount of waste. Moreover, at least some used paper towels may be inadvertently dropped onto a floor, left on a counter, or the like within the lavatory.

Known commercial hand dryers are generally too large, bulky, and noisy for use within a confined lavatory onboard an aircraft. Further, such hand dryers draw a relatively large amount of power.

SUMMARY OF THE DISCLOSURE

A need exists for an efficient hand drying system and method that may be used within a lavatory onboard an aircraft. A need exists for a quiet and sanitary hand drying system and method that generates little to no waste.

With those needs in mind, certain examples of the present disclosure provide a hand drying system for a lavatory. The hand drying system includes a blower housing that includes a blower that is configured to generate airflow within an air chamber. An exhaust vent is configured to be secured to the lavatory. The exhaust vent defines an air outlet. A conduit includes a first end in fluid communication with the air chamber and a second end in fluid communication with the air outlet. The conduit distally locates the blower housing from the lavatory.

Acoustic insulation may be coupled to the blower housing. An acoustic dampening barrier may be disposed within the air chamber. An acoustic dampening barrier may be disposed within the conduit.

In at least one example, the blower includes a magnetic motor, and a propeller magnetically coupled to the magnetic motor.

The hand drying system may include an ultraviolet (UV) light assembly disposed within the blower housing and/or the conduit. The UV light assembly is configured to sanitize the airflow with sanitizing UV light before the airflow passes through the air outlet. The UV light assembly may be positioned proximate to the second end of the conduit.

The hand drying system may include a heating coil disposed within the conduit. The heating coil is configured to heat the airflow before the airflow passes through the air outlet. The heating coil may be positioned proximate to the second end of the conduit.

The hand drying system may include an activation sensor configured to detect a presence of a hand within an activation zone and output a presence signal. The blower may be configured to be activated when the activation sensor detects the presence of the hand within the activation zone.

A dryer control unit may be in communication with various components of the hand drying system, such as the blower. For example, the dryer control unit is configured to control operation of the blower.

Certain examples of the present disclosure provide a hand drying method for a lavatory. The hand drying method includes securing an exhaust vent having an air outlet to the lavatory, fluidly coupling a first end of a conduit to an air chamber of a blower housing, fluidly coupling a second end of the conduit to the air outlet of the exhaust vent, distally locating the blower housing from the lavatory by the fluidly coupling, and generating airflow within the air chamber of the blower housing with a blower.

The hand drying method may also include coupling acoustic insulation to the blower housing, disposing at least one first acoustic dampening barrier within the air chamber, and disposing at least one second acoustic dampening barrier within the conduit.

The hand drying method may include disposing an ultraviolet (UV) light assembly within the conduit, emitting sanitizing UV light into the airflow before the before the airflow passes through the air outlet, and sanitizing the airflow by the emitting.

The hand drying method may include disposing a heating coil within the conduit, and using the heating coil to heat the airflow before the airflow pass through the air outlet.

Certain examples of the present disclosure provide a vehicle that includes an internal cabin, a lavatory within the internal cabin, and a hand drying system for the lavatory.

DETAILED DESCRIPTION OF THE DISCLOSURE

The foregoing summary, as well as the following detailed description of certain examples will be better understood when read in conjunction with the appended drawings. As used herein, an element or step recited in the singular and preceded by the word "a" or "an" should be understood as not necessarily excluding the plural of the elements or steps. Further, references to "one example" are not intended to be interpreted as excluding the existence of additional examples that also incorporate the recited features. Moreover, unless explicitly stated to the contrary, examples "comprising" or "having" an element or a plurality of elements having a particular condition may include additional elements not having that condition.

Examples of the present disclosure provide efficient, quiet, and sanitary hand drying systems and methods, such as may be used within lavatories onboard an aircraft. The hand drying systems and method generate substantially less noise than typical hand dryers, and draw a low level of power (as compared to typical hand dryers). The hand drying systems and methods utilize an efficient blower, which may include a propeller that is magnetically coupled to a magnetic motor. In at least one example, the blower includes a propeller, such as a propeller that is used for a radio-controlled (RC) aircraft, that is operatively coupled to a high performance motor. For example, a magnetic motor that is operatively coupled to a propeller provides a compact and highly efficient system. A heating element (such as a heating coil) may be disposed within an air path proximate to an air outlet. Generated noise is minimized or otherwise reduced by disposing the blower in an acoustically insulated housing that is distally located from the air outlet within the lavatory. For example, the housing may be positioned behind a wall of the lavatory and coupled to the air outlet through one or more air ducts.

In at least one example, an ultraviolet (UV) light assembly is disposed within an air path between the housing and the air outlet. Optionally, the UV light assembly may be disposed within the housing. The UV light assembly is configured to emit UV light (such as far UV light) into a flowing airstream before the air stream passes out of the air outlet. The emitted UV light sterilizes the air before the air passes out of the air outlet. In at least one example, the UV light assembly is configured to sterilize internal surfaces of the housing and/or the air path between the housing and the air outlet.

Figure 1:
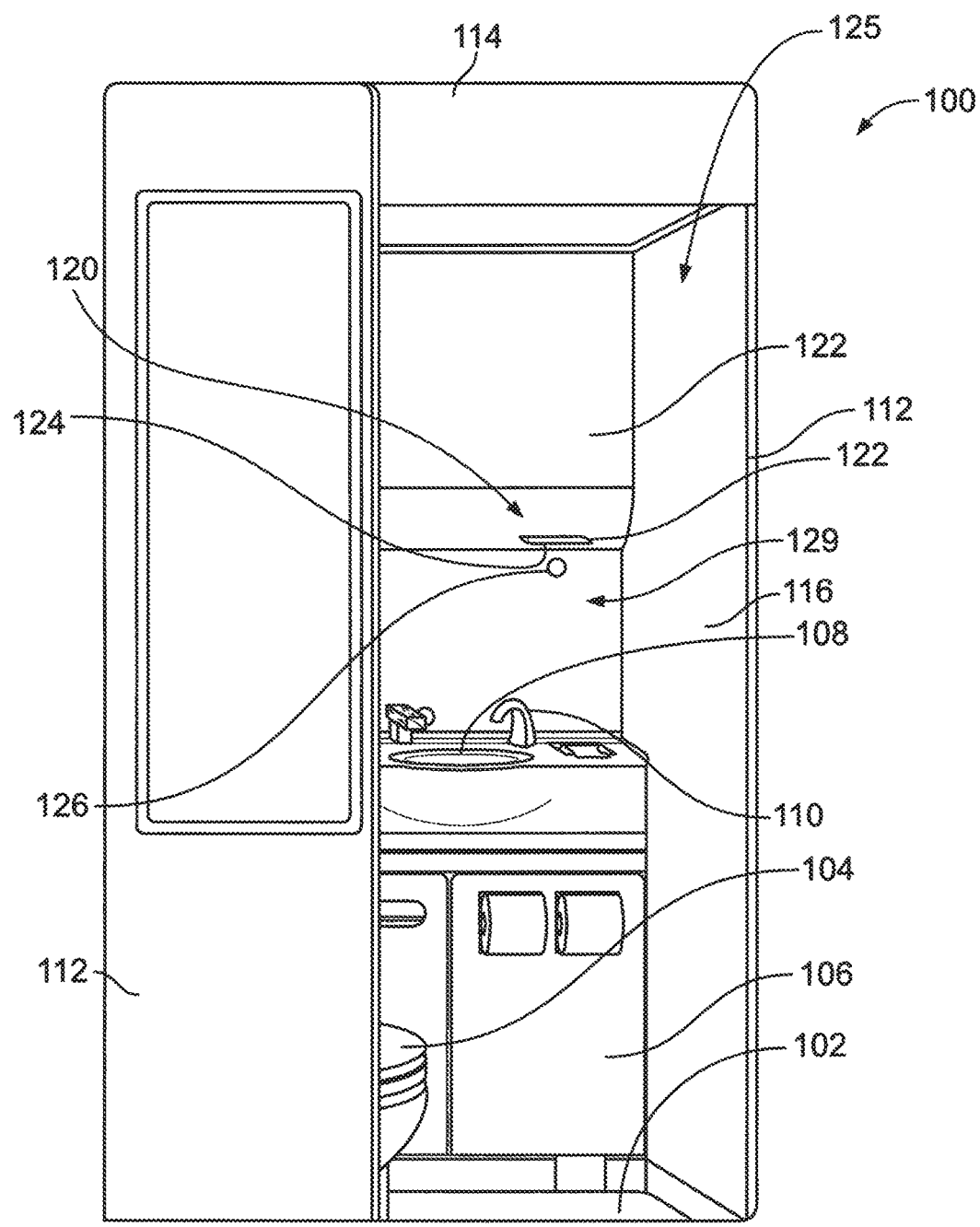
FIG. 1 illustrates a perspective internal view of a lavatory, according to an example of the present disclosure.

FIG. 1 illustrates a perspective internal view of a lavatory 100, according to an example of the present disclosure. The lavatory 100 may be onboard an aircraft, for example. Optionally, the lavatory 100 may be onboard various other vehicles, such as automobiles, buses, locomotives and train cars, ships, watercraft, and the like. In other examples, the lavatory 100 may be within a fixed structure, such as a commercial or residential building, or outbuilding.

The lavatory 100 includes a floor 102 that supports a toilet 104, cabinets 106, a sink 108, and a faucet 110. The lavatory 100 is enclosed by walls 112 that connect to the floor 102 and a ceiling 114. A threshold 116 is formed through one of the walls 112, and is configured to retain a door (not shown in FIG. 1), which is moveable between open and closed positions.

A hand drying system 120 includes an exhaust vent 122 defining an air outlet 124 that is formed or otherwise coupled to one of the walls 112, proximate to the sink 108 and the faucet 110. For example, the exhaust vent 122 may be mounted over the faucet 110, and/or to one side thereof in order to provide a short path between the faucet 110, where hands are washed, and the exhaust vent 122, where wet hands are dried. The air outlet 124 of the exhaust vent 122 is in direct fluid communication with an interior space 125 of the lavatory 100.

An activation sensor 126 is positioned proximate to the exhaust vent 122, such as below the air outlet 124. The activation sensor 126 may be connected to a power source (such as the power source 148 shown in FIG. 3) through one or more wired connections. For example, the activation sensor 126 may be positioned 1-3 inches below the air outlet 124, although the activation sensor 126 may be positioned less than one inch or more than 3 inches below the air outlet 124. In at least one example, the activation sensor 126 is an infrared sensor that is configured to detect presence of an object (such a hand of an individual) within a predetermined activation zone 129 (for example, within 6 radial inches or less of the air outlet 124). The activation zone 129 may be at various locations with the lavatory 100. For example, the activation zone 129 may be underneath the vent 122, above the vent 122, off to a side of the vent 122, or positioned on another structure within the lavatory 100. When the activation sensor 126 detects the presence of a hand within the activation zone 129, the hand drying system 120 is activated to exhaust a drying flow of air out of the air outlet 124. When the hand is removed from the activation zone 129, the activation sensor 126 detect that no hand is within the activation zone, and the hand drying system 120 deactivates. In at least one other example, the activation sensor 126 may be an ultrasonic sensor or other types of sensors that are used to detect presence of an object within a volume of space. Alternatively, instead of an activation sensor, the hand drying system 120 may include an activation button that an individual presses to activate the hand drying system 120 for a predetermined period of time.

Figure 2:
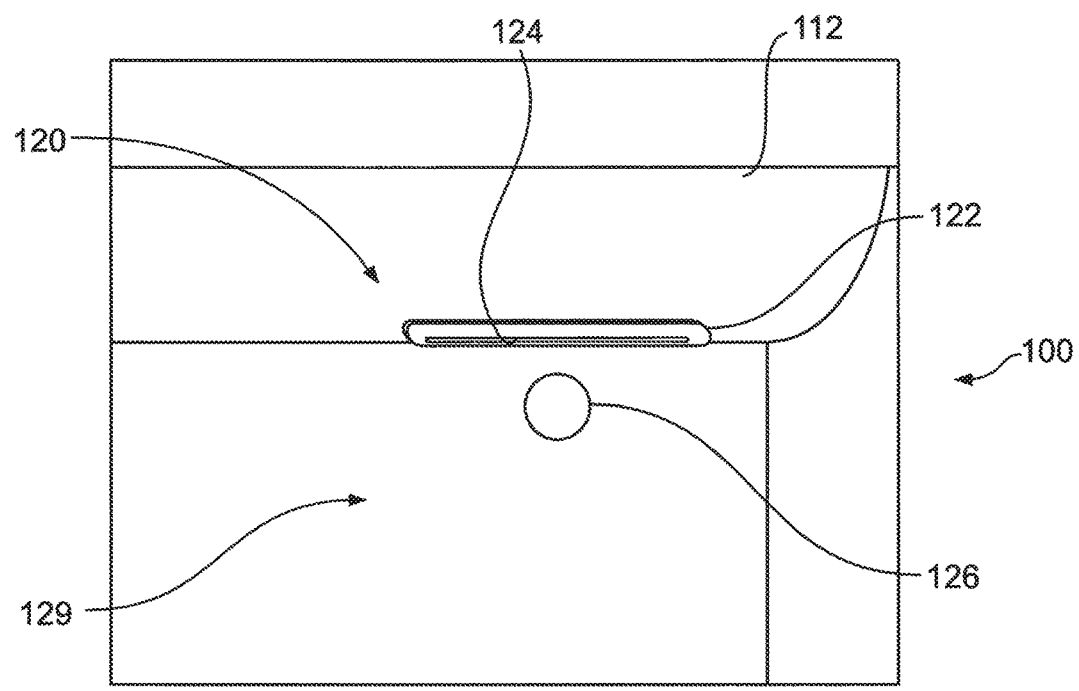
FIG. 2 illustrates a perspective front view of an exhaust vent of a hand drying system mounted in a wall of a lavatory, according to an example of the present disclosure.

FIG. 2 illustrates a perspective front view of the exhaust vent 122 of the hand drying system 120 mounted to the wall 112 of the lavatory 100, according to an example of the present disclosure. As shown, the activation sensor 126 may be secured a short distance (such as between 1-3 inches) underneath the exhaust vent 122. The activation sensor 126 outputs emissions (such as infrared light) over a predetermined distance that defines the activation zone 129. As a hand is moved into the activation zone, the hand drying system 120 activates, thereby exhausting a drying flow of air out of the air outlet 124 of the exhaust vent 122. After the hand is removed from the activation zone 129, the hand drying system 120 deactivates.

Figure 3:
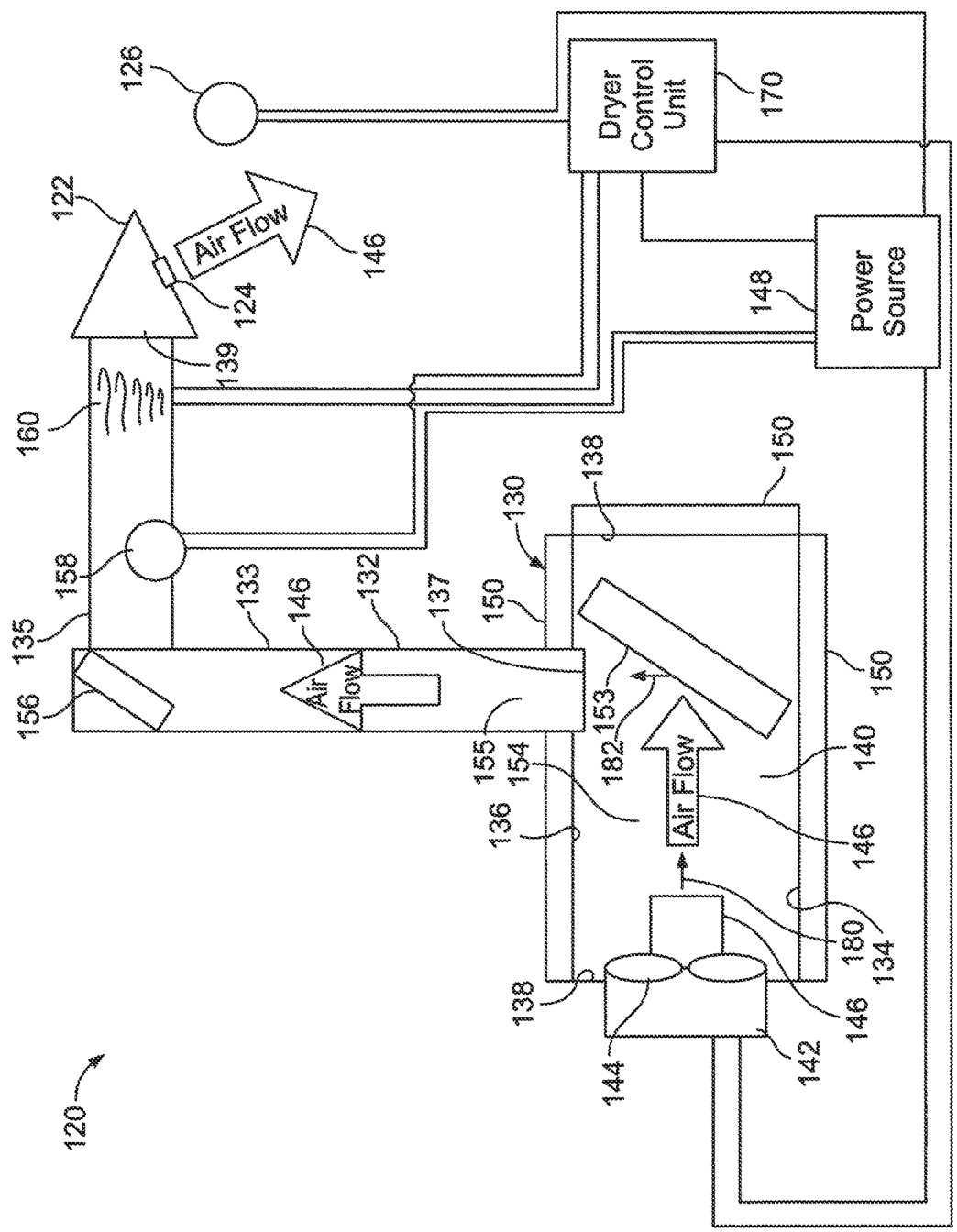
FIG. 3 illustrates a schematic diagram of a hand drying system, according to an example of the present disclosure.

FIG. 3 illustrates a schematic diagram of the hand drying system 120, according to an example of the present disclosure. The hand drying system 120 includes a blower housing 130 connected to the exhaust vent 122 through an airflow conduit 132, such as one or more tubes, pipes, ducts, plenums, or the like.

The blower housing includes a blower 142 that is configured to generate airflow 146 (that is, a flowing stream of air that moves from an air chamber 140 through the conduit 132, and toward and out of the air outlet 124). The exhaust vent 122 is configured to be secured to the lavatory 100 (shown in FIG. 1), such as a wall 112 of the lavatory. The exhaust vent 122 defines the air outlet 124. The conduit 132 has a first end 137 in fluid communication with the air chamber 140, and a second end 139 in fluid communication with the air outlet 124 of the exhaust vent 122.

The blower housing 130 includes a base 134 connected to an upper wall 136 by upstanding support walls 138. The air chamber 140 is defined between the base 134, the upper wall 136, and the support walls 138. The blower 142 is securely mounted to a portion of the blower housing 130. For example, the blower 142 may be securely mounted to a support wall 138, the base 134, and/or the upper wall 136. The blower 142 includes a fan 144 that is operatively coupled to a motor 146. In at least one example, the fan 144 is or otherwise includes a propeller, such as an RC aircraft propeller. In at least one example, the motor 146 is a direct current, magnetic motor that includes one or more permanent magnets that magnetically couple to magnetic material on or within the fan 144. It has been found that a fan 144 in the form of an RC aircraft propeller magnetically coupled to the motor 146 provides a highly energy efficient (upwards of 90% efficiency) and quiet blower 142 (compared to conventional hand dryers) that draws substantially less power than a typical automatic hand dryer. As the magnets of the motor 146 rotate, the magnetic coupling causes the fan 144 to rotate and thereby generate airflow within the air chamber 140. Alternatively, the fan 144 may be or include other types of rotary fans having blades, wheels, or the like, instead of an RC propeller. Also, alternatively, the motor 146 may be another type of actuator (such an electromechanical motor) that operatively couples to the fan through one or more mechanical links, for example.

The motor 146 is coupled to a power source 148, such as through one or more wired connections. In at least one example, the power source 148 is a source of direct current (DC) power, such as one or more batteries. Optionally, the power source 148 may be another source of DC power, or alternating current (AC) power (such as a wall outlet coupled to a standard source of AC power), such as within an aircraft.

Acoustic insulation 150 may be coupled to (for example, mounted on or in, embedded within, and/or the like) the blower housing 130. For example, the acoustic insulation 150 may mount over or under, embed within, line, or be otherwise connected to the base 134, the upper wall 136, and the support walls 138. The acoustic insulation may be acoustic foam, such as closed cell or open cell acoustic foam. Additionally, an acoustic dampening barrier 153 may be mounted within the air chamber 140. The acoustic dampening barrier 153 may be formed of the same material as the acoustic insulation 150. The acoustic dampening barrier 153 is disposed within an air flow path 154 that extends through the air chamber 140 and connects to an interior air channel 155 of the conduit 132. For example, the acoustic dampening barrier 153 is angled to dampen acoustic energy and reflect acoustic waves towards another acoustic dampening barrier 156 secured within the conduit 132. The angle of the dampening barrier 153 may be greater or less than shown. In at least one other example, one or more interior surfaces of the blower housing 130 and/or the conduit 132 may be lined with acoustic insulation.

The conduit 132 may be formed from one or more flexible tubes, pipes, plenums, and/or the like. As shown, the conduit 132 includes a first segment 133 connected to a second segment 135, such as at a right angle. Optionally, the first segment 133 may connect to the second segment 135 at various other angles, arcuate bends, or the like. The acoustic dampening barrier 156 is located at a junction of the first segment 133 and the second segment 135. The conduit 132 may include additional segments. In at least one other example, the conduit 132 may include a single, linear segment that couples the blower housing 130 to the exhaust vent 122.

Referring to FIGS. 1 and 3, the conduit 132 connects the blower housing 130 to the exhaust vent 122, which connects to a wall 112 of the lavatory 100. The conduit 132 allows the blower housing 130 to be distally located from the lavatory 100. For example, the blower housing 130 may be positioned behind a wall 112, under the floor 102, or above the ceiling 114 of the lavatory 100. In at least one example, the blower housing 130 does not contact any portion of the lavatory 100. By distally locating the blower housing 130 from the lavatory 100, noise generated by the hand drying system 120 does not transmit into the lavatory 100. Further, the acoustic insulation 150 and the acoustic dampening barriers 153 and 156 dampen (for example, absorbs) sound waves before they reach the exhaust vent 122.

A UV light assembly 158 is secured within the conduit 132 proximate to the exhaust vent 122. The UV light assembly 158 is connected to the power source 148, such as through one or more wired connections. The UV light assembly 158 is configured to emit sanitizing UV light into an airstream that flows through the conduit 132 towards the exhaust vent 122. In so doing, the airstream is sterilized by the sanitizing UV light before it exhausts through the air outlet 124. As shown, the UV light assembly 158 is within the conduit 132. Therefore, emitted UV light may not pass out of the air outlet 124. In this manner, an individual within the lavatory 100 (shown in FIGS. 1 and 2) generally does not see the UV light assembly 158 or the generated sanitizing UV light. In this configuration, the individual is not directly exposed to the emitted sanitizing UV light. Optionally, the UV light assembly 158 may be disposed within the blower enclosure 130 and/or proximate to the end 137 of the conduit 132. In at least one other example, the hand drying system 120 may include multiple UV light assemblies 158.

In at least one example, the sanitizing UV light is far UV light. Alternatively, the sanitizing UV light may be UVA light, UVB light, UVC light, vacuum UV light, or the like. In at least one example, the UV light assembly 158 includes one or more UV light elements, such as an air lamp, light emitting diodes (LEDs), filaments, fiber optics, and/or the like that are configured to emit the sanitizing UV light. In at least one example, the UV light elements may be configured to emit UV light with different UV bands (for example, at different wavelengths and different frequencies). For example, one UV light element may be configured to emit far UV light, while another UV light element may be configured to emit UVC light. Alternatively, the hand drying system 120 may not include the UV light assembly 158.

A heating coil 160 is disposed within the conduit 132 proximate to the exhaust vent 122, and is connected to the power source 148, such as through one or more wired connections. As shown, the heating coil 160 may be disposed within the conduit 132 between the UV light assembly 158 and the exhaust vent 122. By positioning the heating coil 160 close to the vent, the airstream that flows through the conduit 132 is heated just prior to passing out of the air outlet 124. In this manner, the airstream that passes out of the air outlet 124 is ensured to be warm, as compared to if the heating coil 160 were disposed closer to the blower housing 130. Alternatively, the heating coil 160 may be positioned within the conduit 132 closer to the blower housing 130. In at least one other example, the heating coil 160 may be disposed within the blower housing 130. Optionally, the hand drying system 120 may include a plurality of heating coils disposed within the conduit 132 and/or the blower housing 130. Alternatively, the hand drying system 120 may not include the heating coil 160.

A dryer control unit 170 is in communication with the motor 146, the UV light assembly 158, the heating coil 160, and the activation sensor 126, such as through one or more wired or wireless connections. The dryer control unit 170 may also be connected to the power source 148, such as through one or more wired connections, or may optionally include a separate power source. The dryer control unit 170 may be mounted to a portion of the hand drying system 120 (such as to the blower housing 130) or may be remotely located from the other components of the hand drying system 120. The dryer control unit 170 may be connected to the power source 148, or powered by another source of power. The dryer control unit 170 is configured to control operation of the hand drying system 120.

Referring to FIGS. 1-3, in operation, in order for individuals to dry their hands, the individuals position their hands within the activation zone 129 of the activation sensor 126. As the hand(s) is positioned within the activation zone 129, the activation sensor 126 detects the presence thereof (such as through infrared radiation), and emits a presence signal to the dryer control unit 170. Upon receiving the presence signal from the activation sensor 126, the dryer control unit 170 activates the motor 146, which causes the fan 144 to rotate and thereby generate the airflow 146 within the air chamber 140.

Noise generated by the blower 142 is reduced (for example, dampened) by the acoustic insulation 150 coupled to the blower housing 130. Further, noise generated by the blower 142 within the air chamber 142 is emitted as an acoustic wave 180 that propagates towards the acoustic dampening barrier 153. The acoustic energy of the wave 180 is further dampened by the acoustic dampening barrier 153. Residual acoustic energy 182 may reflect off the acoustic dampening barrier 153 towards the acoustic dampening barrier 156. The acoustic dampening barrier 153 is angled within the air chamber 140 such that the residual acoustic energy 182 is reflected towards the acoustic dampening barrier 156 (for example, the angle of incidence equals the angle of reflectance). Because the residual acoustic energy 182 is linearly reflected toward the acoustic dampening barrier 156, the conduit 132 need not be fully insulated with acoustic insulation. Instead, the acoustic dampening barrier 156 is disposed at the junction of the first and second segments 133 and 135, and thereby dampens (for example, absorbs) the residual acoustic energy 182, ensuring that any noise generated by the blower 142 is substantially dampened or otherwise reduced. Alternatively, additional acoustic insulation may be coupled to the conduit 132. Because the blower housing 130 is disposed away from the lavatory 100 by the conduit 132, any noise generated by the blower 142 is dampened before reaching the lavatory 100 by virtue of the distance between the blower housing 140 and the lavatory 100, and the acoustic insulation 150 and the acoustic dampening barriers 153 and 156.

As the airflow 146 passes through the conduit 132, the dryer control unit 170 activates the UV light assembly 158 to sanitize the flowing air before the airflow 146 exhaust out of the air outlet 124 onto the hand(s). In this manner, the airflow 146 is sanitized before passing onto the hand(s) that are being dried.

Further, the dryer control unit 170 operates the heating coil 160 to heat the airflow 146 before it exhaust out of the air outlet 124. Accordingly, the airflow 146 is heated before passing onto the hands(s) that are being dried, thereby increasing the rate of drying.

After the hand(s) are removed from the activation zone 129, the activation sensor 126 detects that nothing is within the activation zone 129 and sends a corresponding presence signal to the dryer control unit 170. Upon receiving the presence signal indicating nothing within the activation zone 129 from the activation sensor 126, the dryer control unit 170 deactivates the motor 146, thereby ceasing rotation of the fan 144, and deactivates the UV light assembly 158 and the heating coil 160.

As described above, the hand drying system 100 reduces noise generated by the blower 142 by positioning the blower 142 in the acoustically insulated housing 130 and distally away from the lavatory 100 (such as behind a wall of the lavatory 100). The acoustic dampening barrier 156 is positioned within a right angle bend of the conduit 132, and dampens the residual acoustic energy 182. In at least one example, the fan 144 is a highly efficient RC aircraft propeller coupled to the motor 146, which may be a permanent magnet motor, which generates substantially less noise than typical automatic hand dryers. The hand drying system 100 also provides increased sanitation through the use of the UV light assembly 156, which sanitizes the airflow 146 before it exhaust out of the air outlet 124, and touchless operation via the activation sensor 126 in communication with the dryer control unit 170.

As used herein, the term "control unit," "central processing unit," "CPU," "computer," or the like may include any processor-based or microprocessor-based system including systems using microcontrollers, reduced instruction set computers (RISC), application specific integrated circuits (ASICs), logic circuits, and any other circuit or processor including hardware, software, or a combination thereof capable of executing the functions described herein. Such are exemplary only, and are thus not intended to limit in any way the definition and/or meaning of such terms. For example, the dryer control unit 170 may be or include one or more processors that are configured to control operation of the hand drying system 120, as described above.

The dryer control unit 170 is configured to execute a set of instructions that are stored in one or more data storage units or elements (such as one or more memories), in order to process data. For example, the dryer control unit 170 may include or be coupled to one or more memories. The data storage units may also store data or other information as desired or needed. The data storage units may be in the form of an information source or a physical memory element within a processing machine.

The set of instructions may include various commands that instruct the dryer control unit 170 as a processing machine to perform specific operations such as the methods and processes of the various examples of the subject matter described herein. The set of instructions may be in the form of a software program. The software may be in various forms such as system software or application software. Further, the software may be in the form of a collection of separate programs, a program subset within a larger program, or a portion of a program. The software may also include modular programming in the form of object-oriented programming. The processing of input data by the processing machine may be in response to user commands, or in response to results of previous processing, or in response to a request made by another processing machine.

The diagrams of examples herein may illustrate one or more control or processing units, such as the dryer control unit 170. It is to be understood that the processing or control units may represent circuits, circuitry, or portions thereof that may be implemented as hardware with associated instructions (e.g., software stored on a tangible and non-transitory computer readable storage medium, such as a computer hard drive, ROM, RAM, or the like) that perform the operations described herein. The hardware may include state machine circuitry hardwired to perform the functions described herein. Optionally, the hardware may include electronic circuits that include and/or are connected to one or more logic-based devices, such as microprocessors, processors, controllers, or the like. Optionally, the dryer control unit 170 may represent processing circuitry such as one or more of a field programmable gate array (FPGA), application specific integrated circuit (ASIC), microprocessor(s), and/or the like. The circuits in various examples may be configured to execute one or more algorithms to perform functions described herein. The one or more algorithms may include aspects of examples disclosed herein, whether or not expressly identified in a flowchart or a method.

As used herein, the terms "software" and "firmware" are interchangeable, and include any computer program stored in a data storage unit (for example, one or more memories) for execution by a computer, including RAM memory, ROM memory, EPROM memory, EEPROM memory, and non-volatile RAM (NVRAM) memory. The above data storage unit types are exemplary only, and are thus not limiting as to the types of memory usable for storage of a computer program.

Figure 4:
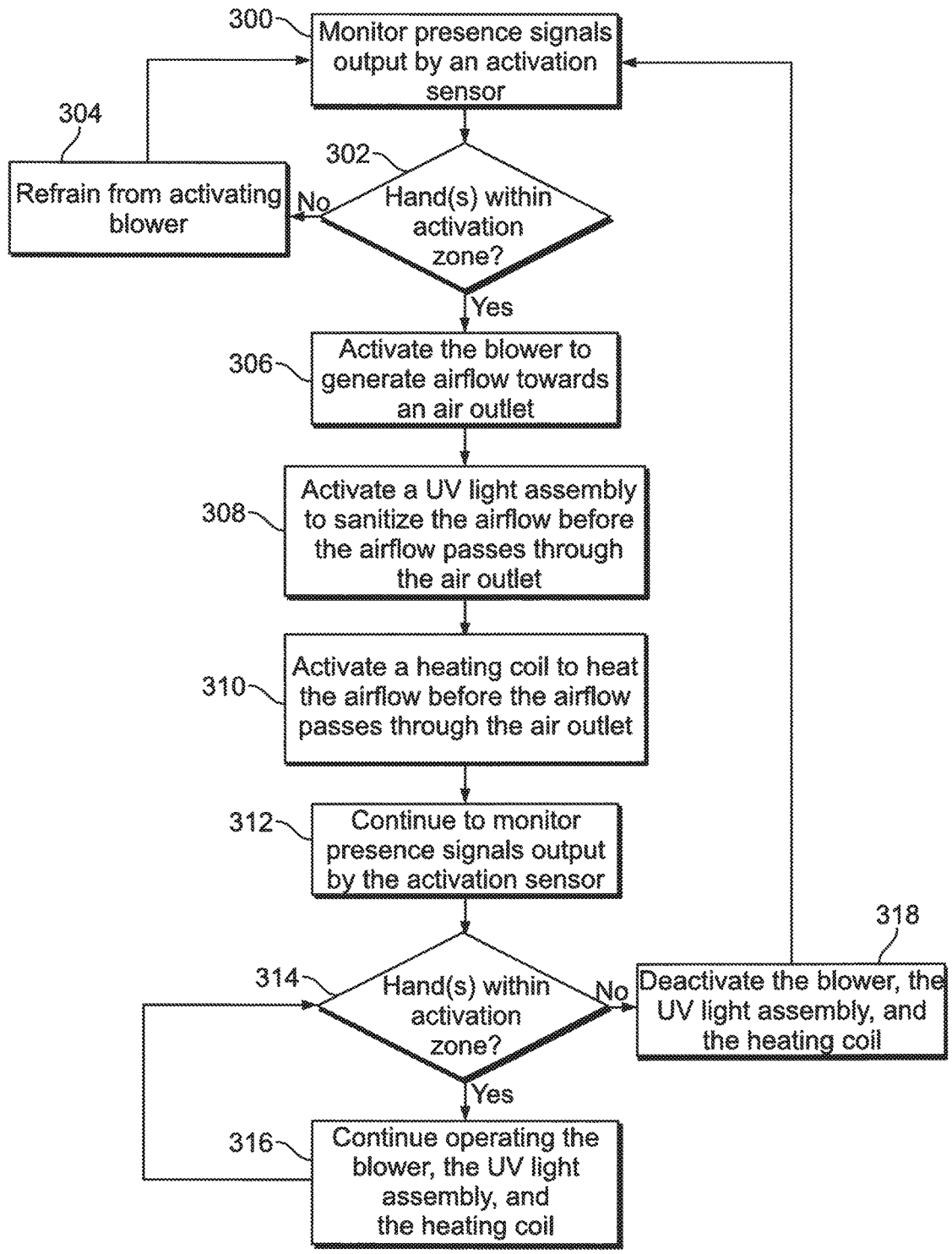
FIG. 4 is a flow chart of a method of operating a hand drying system, according to an example of the present disclosure.

FIG. 4 is a flow chart of a method of operating a hand drying system, according to an example of the present disclosure. Referring to FIGS. 1-4, the method begins at 300, at which the dryer control unit 170 receives and monitors presence signals output by the activation sensor 126. At 302, the dryer control unit 170 determines whether a hand is within an activation zone of the activation sensor 126, based on the presence signals received from the activation sensor 126. If a hand is not within the activation zone, the dryer control unit 170 refrains from activating the blower 142 at 304. The method then returns to 300.

If, however, the dryer control unit 170 determines that a hand is within the activation zone, the method proceeds from 302 to 306, at which the dryer control unit 170 activates the blower 142 to generate airflow 146 in the air chamber 140 and the conduit 132 towards the air outlet 124. At 308, the dryer control unit 170 activates the UV light assembly 158 to sanitize the airflow 146 before the airflow 146 passes through the air outlet 124. At 310, the dryer control unit 170 activates the heating coil 160 to heat the airflow before the airflow passes through the air outlet 124.

At 312, the dryer control unit 170 continues to monitor the presence signals output by the activation sensor 126. At 314, the dryer control unit 170 determines whether the hand(s) is still within the activation zone, based on the presence signals received from the activation sensor 126. If the hand(s) is still within the activation zone, the method proceeds from 314 to 316, at which the dryer control unit 170 continues to operate the blower 142, the UV light assembly 158, and the heating coil 160. The method then returns to 314.

If, however, the dryer control unit 170 determines at 314 that the hand(s) is no longer within the activation zone, the method proceeds to 318, at which the dryer control unit 170 deactivates each of the blower 142, the UV light assembly 158, and the heating coil 160. The method then returns to 300.

Figure 5:
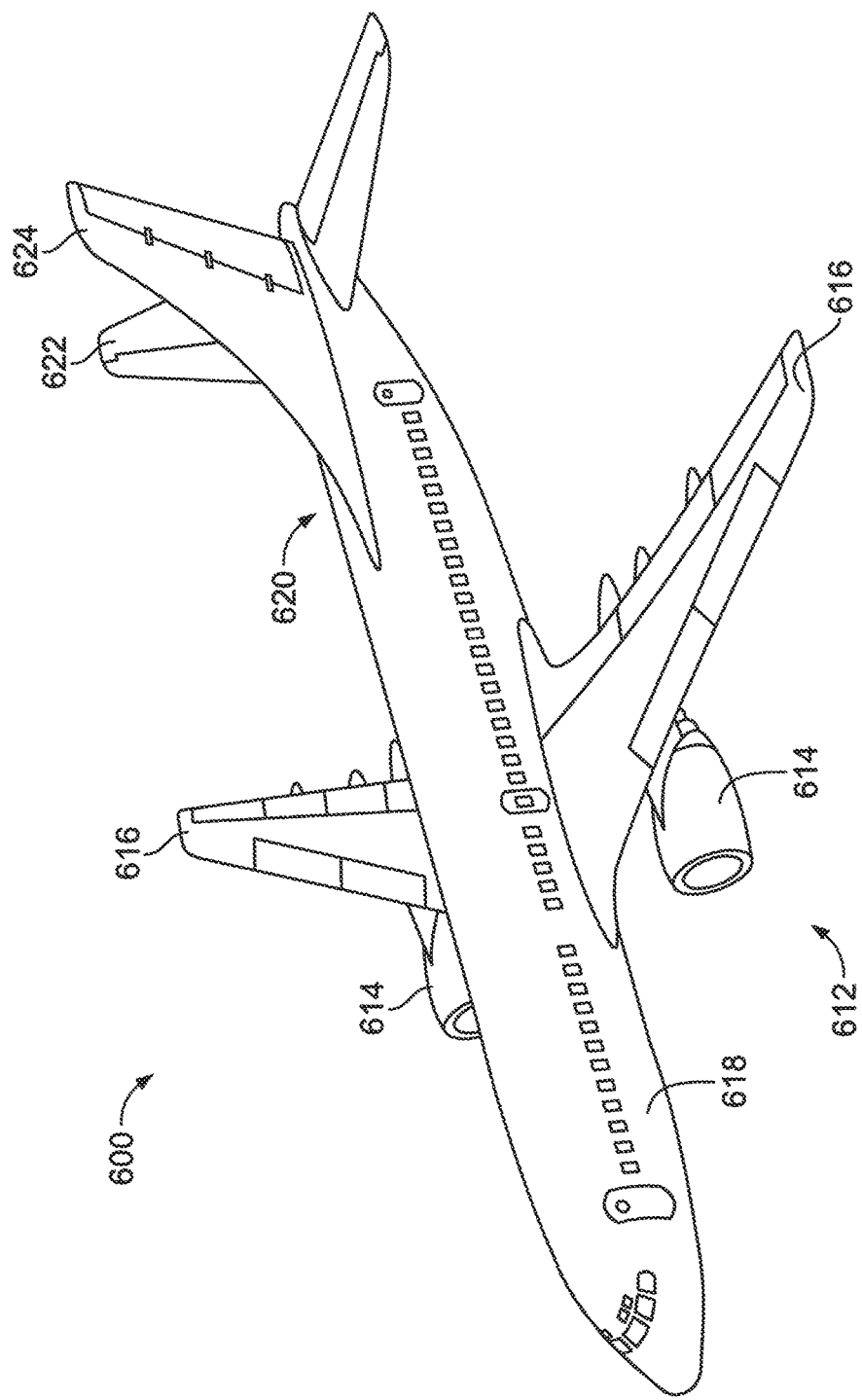
FIG. 5 illustrates a perspective top view of an aircraft, according to an example of the present disclosure.

FIG. 5 illustrates a perspective top view of an aircraft 600, according to an example of the present disclosure. The aircraft 600 includes a propulsion system 612 that may include two turbofan engines 614, for example. Optionally, the propulsion system 612 may include more engines 614 than shown. The engines 614 are carried by wings 616 of the aircraft 600. In other examples, the engines 614 may be carried by a fuselage 618 and/or an empennage 620. The empennage 620 may also support horizontal stabilizers 622 and a vertical stabilizer 624.

The fuselage 618 of the aircraft 600 defines an internal cabin, which may include a cockpit, one or more work sections (for example, galleys, personnel carry-on baggage areas, and the like), one or more passenger sections (for example, first class, business class, and coach sections), and an aft section. Each of the sections may be separated by a cabin transition area, which may include one or more class divider assemblies. Overhead stowage bin assemblies may be positioned throughout the internal cabin. The internal cabin includes lavatories 100 (shown in FIGS. 1 and 2). A hand drying system 120 (shown in FIGS. 1-3) is disposed within each lavatory 100.

Alternatively, instead of an aircraft, examples of the present disclosure may be used with various other vehicles, such as automobiles, buses, recreational vehicles, locomotives and train cars, ships, watercraft, and the like. Further, examples of the present disclosure may be used with respect to fixed structures, such as commercial and residential buildings, or outbuildings.

Figure 6:
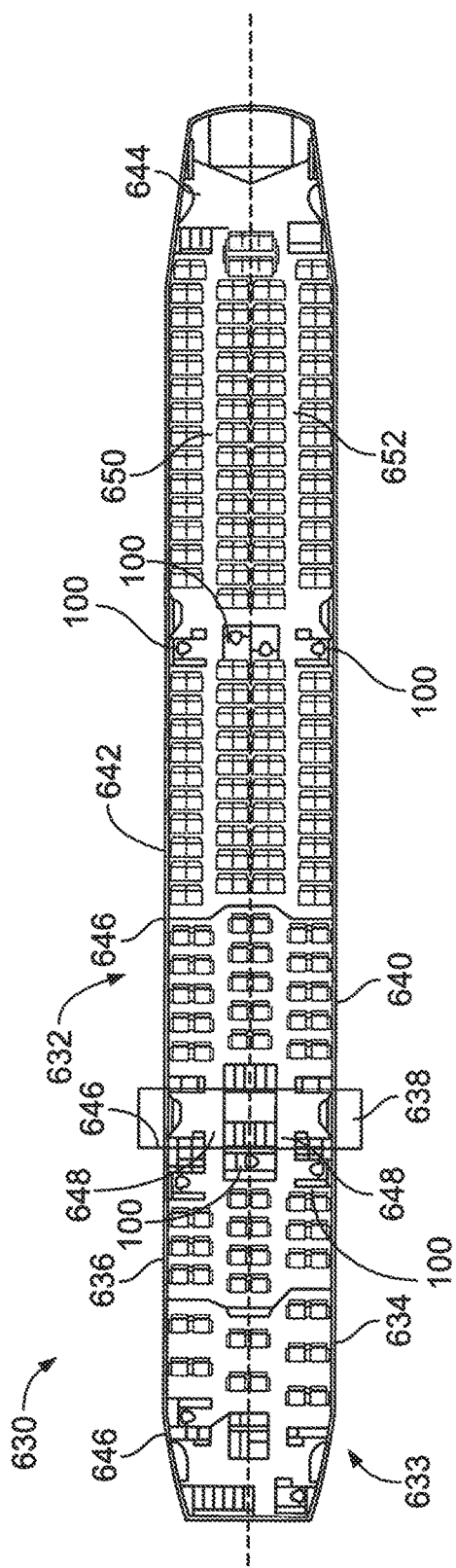
FIG. 6 illustrates a top plan view of an internal cabin of an aircraft, according to an example of the present disclosure.

FIG. 6 illustrates a top plan view of an internal cabin 630 of an aircraft, according to an example of the present disclosure. The internal cabin 630 may be within a fuselage 632 of the aircraft. For example, one or more fuselage walls may define the internal cabin 630. The internal cabin 630 includes multiple sections, including a front section 633, a first class section 634 (or first class suites, cabins, for example), a business class section 636, a front galley station 638, an expanded economy or coach section 640, a standard economy or coach section 642, and an aft section 644, which may include multiple lavatories 100, each of which may include a hand drying system 120 (shown in FIGS. 1-3), as described above. It is to be understood that the internal cabin 630 may include more or less sections than shown. For example, the internal cabin 630 may not include a first class section, and may include more or less galley stations than shown. Each of the sections may be separated by a cabin transition area 646, which may include class divider assemblies between aisles 648.

As shown in FIG. 6, the internal cabin 630 includes two aisles 650 and 652 that lead to the aft section 644. Optionally, the internal cabin 630 may have less or more aisles than shown. For example, the internal cabin 630 may include a single aisle that extends through the center of the internal cabin 630 that leads to the aft section 644.

Figure 7:
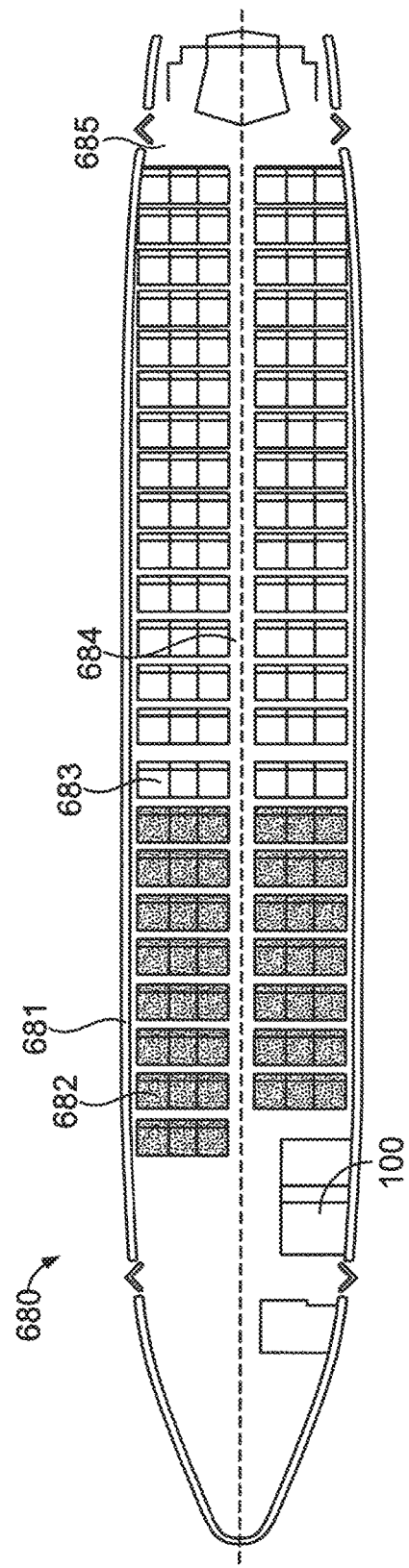
FIG. 7 illustrates a top plan view of an internal cabin of an aircraft, according to an example of the present disclosure.

FIG. 7 illustrates a top plan view of an internal cabin 680 of an aircraft, according to an example of the present disclosure. The internal cabin 680 may be within a fuselage 681 of the aircraft. For example, one or more fuselage walls may define the internal cabin 680. The internal cabin 680 includes multiple sections, including a main cabin 682 having passenger seats 683, and an aft section 685 behind the main cabin 682. It is to be understood that the internal cabin 680 may include more or less sections than shown.

The internal cabin 680 may include a single aisle 684 that leads to the aft section 685. The single aisle 684 may extend through the center of the internal cabin 680 that leads to the aft section 685. For example, the single aisle 684 may be coaxially aligned with a central longitudinal plane of the internal cabin 680.

One or more lavatories 100 may be located within the internal cabin 680. Each lavatory 100 may include a hand drying system 120 (shown in FIGS. 1-3), as described above.

Figure 8:
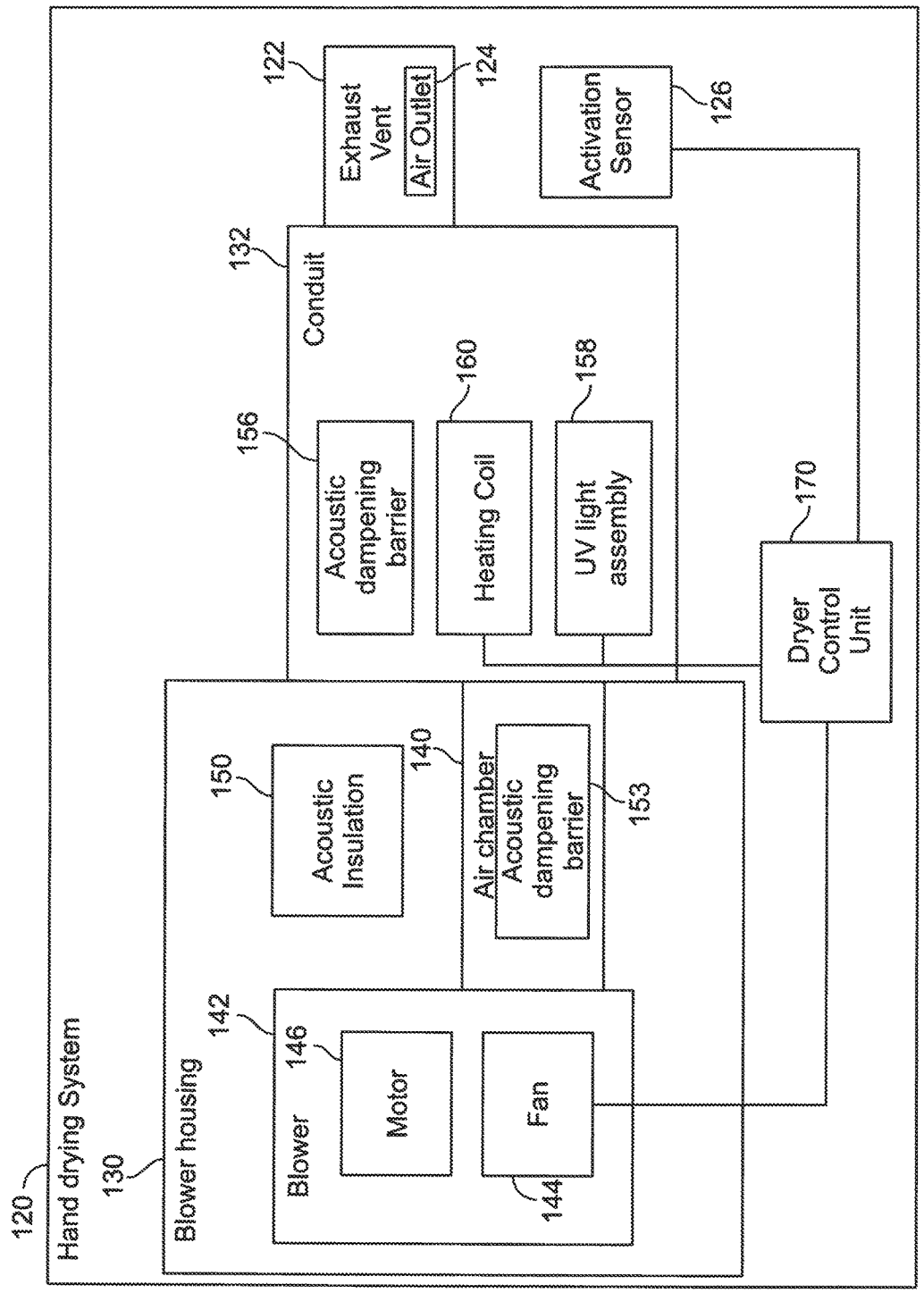
FIG. 8 illustrates a nested block diagram of a hand drying system, according to an example of the present disclosure.

FIG. 8 illustrates a nested block diagram of the hand drying system 120, according to an example of the present disclosure. The hand drying system 120 may be used in a lavatory 100, such as any of the lavatories within the internal cabin 630 (shown in FIG. 6) or the internal cabin 680 (shown in FIG. 7). The hand drying system 120 includes the blower housing 130, which includes the blower 142 that generates airflow within the air chamber 140. In at least one example, the blower 142 includes the motor 146, such as a magnetic motor, and the fan 144, such as a propeller magnetically coupled to the magnetic motor.

The exhaust vent 122 defines the air outlet 124, which may be in fluid communication with an internal space of a lavatory, for example.

The conduit 132 is in fluid communication with the air chamber 140 and the air outlet 124. The conduit 132 distally locates the blower housing 130 from the internal space of the lavatory.

Acoustic insulation 150 may be coupled to the blower housing 130. At least one acoustic dampening barrier 153 may be disposed within the air chamber 140. At least one acoustic dampening barrier 156 may be disposed within the conduit 132. The acoustic insulation 150 and the acoustic dampening barriers 153 and 156 reduce noise generated by the blower 142.

A heating coil 160 may be disposed within the conduit 132. The heating coil 160 is configured to heat the airflow before the airflow passes through the air outlet 124 into the internal space of the lavatory.

An activation sensor 126 is configured to detect a presence of a hand within an activation zone and output a presence signal that is input into a dryer control unit 170. That is, the dryer control unit 170 receives the presence signal. The blower 142 is configured to be activated when the activation sensor 126 detects the presence of the hand within the activation zone. For example, in response to receiving the presence signal, the dryer control unit activates the blower 142.

The dryer control unit 170 is in communication with the blower 142, the heating coil 160, and the activation sensor 126. The dryer control unit 170 is configured to control operation of the hand drying system 120.

In at least one example, the hand drying system 120 includes the ultraviolet (UV) light assembly 158 disposed within the blower housing 130 and/or the conduit 132. The UV light assembly 158 sanitizes the airflow with sanitizing UV light before the airflow passes through the air outlet 124.

Referring to FIGS. 1-8, examples of the present disclosure provide efficient hand drying systems and methods that are particularly well-suited for use within a lavatory onboard an aircraft. Examples of the present disclosure provide quiet and sanitary hand drying systems and methods that generate little to no waste.

While various spatial and directional terms, such as top, bottom, lower, mid, lateral, horizontal, vertical, front and the like may be used to describe examples of the present disclosure, it is understood that such terms are merely used with respect to the orientations shown in the drawings. The orientations may be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described examples (and/or aspects thereof) may be used in combination with each other. In addition, many modifications may be made to adapt a particular situation or material to the teachings of the various examples of the disclosure without departing from their scope. While the dimensions and types of materials described herein are intended to define the parameters of the various examples of the disclosure, the examples are by no means limiting and are exemplary examples. Many other examples will be apparent to those of skill in the art upon reviewing the above description. The scope of the various examples of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various examples of the disclosure, including the best mode, and also to enable any person skilled in the art to practice the various examples of the disclosure, including making and using any devices or systems and performing any incorporated methods. The patentable scope of the various examples of the disclosure is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A hand drying system for a lavatory, the hand drying system comprising:
   a blower housing that includes a blower that generates airflow within an air chamber, wherein the blower includes a magnetic motor, and a propeller magnetically coupled to the magnetic motor;
   an exhaust vent secured to the lavatory, wherein the exhaust vent defines an air outlet; and
   a conduit having a first end in fluid communication with the air chamber and a second end in fluid communication with the air outlet, wherein the conduit distally locates the blower housing from the lavatory.

2. The hand drying system of claim 1, further comprising acoustic insulation coupled to the blower housing.

3. The hand drying system of claim 1, further comprising an acoustic dampening barrier disposed within the air chamber.

4. The hand drying system of claim 1, further comprising at least one acoustic dampening barrier disposed within the conduit.

5. The hand drying system of claim 1, further comprising an ultraviolet (UV) light assembly disposed within one or both of the blower housing or the conduit, wherein the UV light assembly sanitizes the airflow with sanitizing UV light before the airflow passes through the air outlet.

6. The hand drying system of claim 5, wherein the UV light assembly is positioned proximate to the second end of the conduit, wherein the conduit prevents the UV light from passing out of the air outlet.

7. The hand drying system of claim 1, further comprising a heating coil disposed within the conduit, wherein the heating coil is configured to heat the airflow before the airflow passes through the air outlet.

8. The hand drying system of claim 7, wherein the heating coil is positioned proximate to the second end of the conduit.

9. The hand drying system of claim 1, further comprising an activation sensor configured to detect a presence of a hand within an activation zone and output a presence signal, wherein the blower is configured to be activated when the activation sensor detects the presence of the hand within the activation zone.

10. The hand drying system of claim 1, further comprising a dryer control unit in communication with the blower, wherein the dryer control unit is configured to control operation of the blower.

11. A hand drying method for a lavatory, the hand drying method comprising:
   securing an exhaust vent having an air outlet to the lavatory;
   fluidly coupling a first end of a conduit to an air chamber of a blower housing;
   coupling acoustic insulation to the blower housing;
   disposing at least one first acoustic dampening barrier within the air chamber;
   disposing at least one second acoustic dampening barrier within the conduit
   fluidly coupling a second end of the conduit to the air outlet of the exhaust vent;
   distally locating the blower housing from the lavatory by the fluidly coupling; and
   generating airflow within the air chamber of the blower housing with a blower including a magnetic motor and a propeller magnetically coupled to the magnetic motor.

12. The hand drying method of claim 11, further comprising:
   disposing an ultraviolet (UV) light assembly within the conduit;
   emitting sanitizing UV light into the airflow before the before the airflow passes through the air outlet; and
   sanitizing the airflow by the emitting.

13. The hand drying method of claim 12, wherein the disposing the UV light assembly within the conduit comprises positioning the UV light assembly proximate to the second end of the conduit.

14. The hand drying method of claim 11, further comprising:
   disposing a heating coil within the conduit; and
   using the heating coil to heat the airflow before the airflow pass through the air outlet.

15. The hand drying method of claim 14, wherein the disposing the heating coil within the conduit comprises positioning the heating coil proximate to the second end of the conduit.

16. The hand drying method of claim 11, further comprising:
   operatively coupling a dryer control unit to the blower; and
   using the dryer control unit to control operation of the blower.

17. A vehicle comprising:
an internal cabin;
a lavatory within the internal cabin, wherein the lavatory defines an internal space; and
   a hand drying system for the lavatory, the hand drying system comprising:
   a blower housing that includes a blower that is configured to generate airflow within an air chamber, wherein the blower includes a magnetic motor, and a propeller magnetically coupled to the magnetic motor;
   an exhaust vent secured to the lavatory, wherein the exhaust vent defines an air outlet that is in fluid communication with the internal space of the lavatory;
   a conduit having a first end in fluid communication with the air chamber and a second end in fluid communication with the air outlet, wherein the conduit distally locates the blower housing from the internal space of the lavatory;
   acoustic insulation coupled to the blower housing;
   at least one first acoustic dampening barrier disposed within the air chamber;
   at least one second acoustic dampening barrier disposed within the conduit, wherein the acoustic insulation, the at least one first acoustic dampening barrier, and the at least one second acoustic dampening barrier reduce noise generated by the blower;
   a heating coil disposed within the conduit, wherein the heating coil is configured to heat the airflow before the airflow passes through the air outlet into the internal space of the lavatory, wherein the heating coil is positioned proximate to the second end of the conduit;
   an activation sensor configured to detect a presence of a hand within an activation zone and output a presence signal, wherein the blower is configured to be activated when the activation sensor detects the presence of the hand within the activation zone; and
   a dryer control unit in communication with the blower, the heating coil, and the activation sensor, wherein the dryer control unit is configured to control operation of the hand drying system.

18. The vehicle of claim 17, wherein the hand drying system further comprises an ultraviolet (UV) light assembly disposed within one or both of the blower housing or the conduit, wherein the UV light assembly is configured to sanitize the airflow with sanitizing UV light before the airflow passes through the air outlet into the internal space of the lavatory.

19. The vehicle of claim 18, wherein the UV light assembly is positioned proximate to the second end of the conduit.

* * * * *